United States Patent [19]

Greatbatch

[11] 4,314,554

[45] Feb. 9, 1982

[54] TISSUE GROWTH CONTROL APPARATUS AND METHOD

[76] Inventor: Wilson Greatbatch, 5220 Donnington Rd., Clarence, N.Y. 14031

[21] Appl. No.: 57,744

[22] Filed: Jul. 16, 1979

[51] Int. Cl.³ ............................ A61N 1/30; A61N 1/32
[52] U.S. Cl. ............................ 128/207.21; 128/419 F
[58] Field of Search .............. 128/82.1, 207.21, 419 F, 128/419 B, 419 C, 419 P, 419 R, 420 R

[56] References Cited

U.S. PATENT DOCUMENTS

| | | | |
|---|---|---|---|
| 3,842,841 | 10/1974 | Brighton et al. | 128/419 F |
| 3,955,583 | 5/1976 | Horauf | 128/420 R |
| 4,019,510 | 4/1977 | Ellis | 128/207.21 |
| 4,026,304 | 5/1977 | Levy | 128/419 F |
| 4,027,393 | 6/1977 | Ellis et al. | 128/207.21 |
| 4,109,660 | 8/1978 | Nesmeyanov et al. | 128/419 R |

FOREIGN PATENT DOCUMENTS

| | | | |
|---|---|---|---|
| 707011 | 3/1965 | Canada | 128/419 F |
| 2552523 | 8/1976 | Fed. Rep. of Germany | 128/419 F |
| 632363 | 11/1978 | U.S.S.R. | 128/420 R |
| 643156 | 1/1979 | U.S.S.R. | 128/419 F |

OTHER PUBLICATIONS

Becker et al., "Clinical Experiences . . . Bone Growth", Jour. Clin. Orth., 124:75, 1977.

*Primary Examiner*—Lee S. Cohen
*Attorney, Agent, or Firm*—Christel, Bean & Linihan

[57] ABSTRACT

A method and apparatus for providing germicidal and healing treatment of tissue such as bone wherein an electrode of silver or like material is applied to a living tissue site to be healed, initially a direct voltage is applied to the electrode of a polarity driving the electrode as an anode to release silver ions to create a germicidal environment at the site, and thereafter a direct voltage of opposite polarity is applied to the electrode driving it as a cathode to stimulate healing of the tissue at the site. The apparatus is implanted in the body of a patient, and in one embodiment a battery is connected through a switch to the electrode and a reference electrode, the switch initially connecting the electrode as an anode and thereafter changeable by an external operator such as a magnet to connect the electrode as a cathode. In another embodiment, another electrode and an element cooperate with the treating electrode to form a galvanic couple with the treating electrode to create a germicidal environment and a predetermined time thereafter the arrangement changes to a biogalvanic couple with body fluid to cause healing of the tissue. In either embodiment a wave shaping circuit can be operatively associated with the treating electrode to facilitate external monitoring of the apparatus when implanted.

17 Claims, 5 Drawing Figures

TISSUE GROWTH CONTROL APPARATUS AND METHOD

BACKGROUND OF THE INVENTION

This invention relates to healing and growth control of tissue such as bone, and more particularly to a method and apparatus for providing germicidal and healing treatment of tissue such as bone.

One area of use of the present invention is providing germicidal and healing treatment of live bone at a bone graft site, although the principles of the present invention can be variously applied. Yasuda found in 1955 that a bone fracture area is a region of abnormally high electrical negativity which appeared to be associated with healing, and he along with Bassett found in 1964 that the application of an artifical electric field from a battery accelerated the healing. Becker found in 1963 and 1977 that silver electrodes, when driven positively, produce a germicidal environment, and he also found that electrical anodal currents of up to about 40 microamperes d.c. are beneficial for a germicidal effect but that negative electric currents of as little as one microampere d.c. are adequate for healing.

It would be highly desirably to provide a method and apparatus for tissue growth control which can accelerate the growth of living tissue such as human bone, and which also can create a germicidal environment for curing tissue and bone infections as well as inhibiting the growth of tumors.

SUMMARY OF THE INVENTION

It is, therefore, a primary object of the present invention to provide a new and improved method and apparatus for providing both germicidal and healing treatment of living tissue such as bone.

It is a further object of this invention to provide such method and apparatus wherein the germicidal and healing treatment modes thereof occur during distinct and precisely controllable time periods.

It is a further object of this invention to provide such method and apparatus wherein an effective germicidal environment is created at the tissue site whereupon an effective healing operation occurs thereafter.

It is a further object of this invention to provide such apparatus which is implantable in the body of a patient.

It is a further object of this invention to provide such apparatus which derives electrical energy for its operation through biogalvanic action with body fluids.

It is a further object of this invention to provide such apparatus which is implanted and which is monitored readily from outside the body of a patient.

The present invention provides a method and apparatus for providing germicidal and healing treatment of tissue such as bone wherein there is applied to a living tissue site to be healed an electrode of a material, preferably silver, which releases ions to create a germicidal environment at the site in response to electrical current flow in one direction relative to the electrode and which stimulates healing of tissue at the site in response to electrical current flow in the opposite direction relative to the electrode. Initially, there is applied to the electrode a direct voltage of polarity causing the current flow in one direction to drive the electrode as an anode and release ions to create the germicidal environment at the site. Thereafter, there is applied to the electrode a direct voltage of opposite polarity causing the current flow in the opposite direction to drive the electrode as a cathode to stimulate and promote healing of the tissue at the site. The apparatus preferably is of the type which is implanted in the body of a patient. In one embodiment thereof, a battery is connected to the electrode and to a reference electrode under control of a switch having a first state connecting the electrodes in a manner establishing the germicidal mode of operation and changeable to a second state under control of an external operator such as a magnet which second state connects the electrodes in a manner establishing the healing mode. In another embodiment thereof, the apparatus includes an additional electrode and an element which cooperate to form a galvanic couple with the treating electrode to establish the germicidal mode of operation and which after a predetermined time change to a biogalvanic couple with body fluid to establish the tissue healing mode of operation. In either embodiment, a wave shaping circuit can be operatively associated with the treating electrode to produce a current waveform which is readily discernible by external monitoring equipment.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENTS

Figure 1:
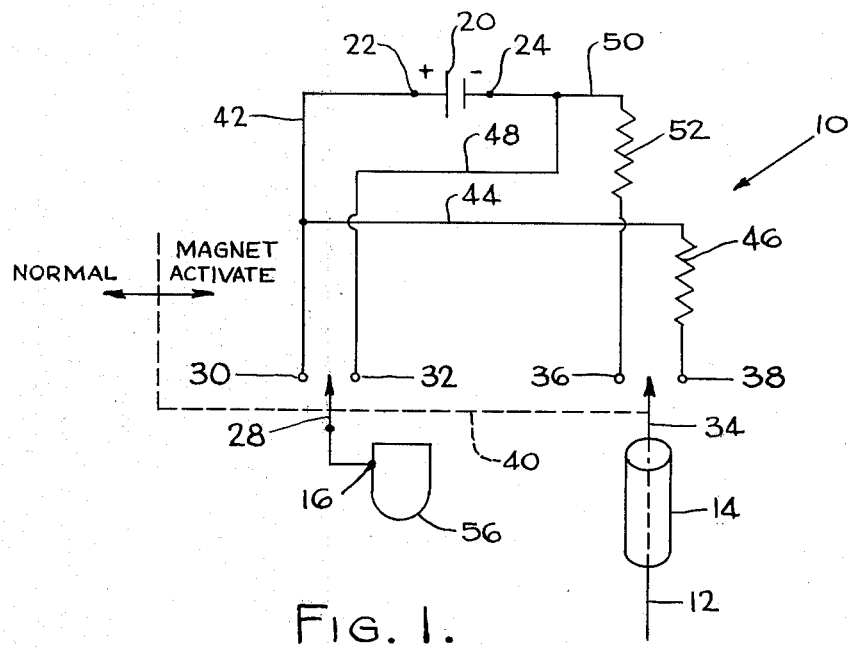
FIG. 1 is a schematic diagram of apparatus according to the present invention.

Referring now to FIG. 1, the apparatus 10 of the present invention for providing germicidal and healing treatment of tissue such as bone comprises a treating electrode in the form of a lead or wire 12 adapted to be placed in operative contact with a living tissue site to be healed. The treating electrode 12 is of a material which releases ions to create a germicidal environment at the site in response to electrical current flow in one direction relative to the treating electrode 12 and which promotes healing of tissue at the site in response to electrical current flow in the opposite direction. According to a preferred mode of the present invention the wire 12 is of silver. A portion of the length of wire 12 is enclosed by a protective covering or sheath 14 of human body reaction-free material such as a suitable silicone rubber material. The sheath 14 serves to allow operative contact between the wire 12 and body tissue only at the site where healing is to take place. The apparatus further comprises another electrode adapted to be connected at a location spaced from the site to be healed. In the apparatus shown in FIG. 1, this electrode is designated 16 and will be described in further detail presently.

The apparatus 10 of the present invention further comprises means for establishing an electrical current flow path between the electrodes and means for applying direct voltage of one polarity to the treating electrode 12 to cause electrical current flow in the one direction to create a germicidal environment at the tissue site and after a predetermined time to apply direct voltage of the opposite polarity to the treating electrode to promote healing of tissue at the site. In particular, the apparatus includes a direct voltage source in a form of a battery 20 having positive and negative polarity output terminals 22 and 24, respectively. Battery 20 is of the type capable of delivering over 2.0 volts, and one form of battery 20 is a lithium-iodine battery of implantable grade and hermetically sealed for use with artifical cardiac pacemakers, available commercially from Wilson Greatbatch Ltd. of Clarence, N.Y. and designated model 752. A switching means is operatively connected to the electrodes and to the terminals of the source. In particular, the switching means comprises a first switch arm 28 movable between a pair of switch contacts 30 and 32. The switching means further comprises a second switch arm 34 movable between a pair of switch contacts 36 and 38. The broken line 40 extending between the switch arms 28 and 34 indicates that the switch is of the type whereby the two switch arms 28 and 34 are moved in unison or together simultaneously between positions engaging the two sets of contacts. In particular, the switching means has a first state wherein switch arm 28 engages contact 32 and switch arm 34 engages contact 38. The switching means has a second state wherein the switch arms 28 and 34 are moved into positions engaging the contacts 30 and 36, respectively. One form of the switching means comprises two implanted single pole, double throw magnetic reed switches driven by a common extracorporeal permanent magnet of the type commonly used with implanted demand cardiac pacemakers to shift the pacemaker from a demand to an asynchronous mode. By way of example, such switches are available commercially from Gordos Corp. of Bloomfield, N.J. under part no. MR 5204-1. The magnet can be any commercially available permanent magnet of the small, hand-held type.

The positive terminal 22 of battery 20 is connected by a lead 42 to switch contact 30. The positive terminal also is connected by a lead 44 to one terminal of a resistor 46, the other terminal of which is connected to switch contact 38. The negative terminal 24 of battery 20 is connected by a lead 48 to switch contact 32. Negative terminal 24 also is connected by a lead 50 to one terminal of a resistor 52, the other terminal of which is connected to the switch contact 36. Thus, the switching means has a first state wherein the silver electrode 12 is connected through resistor 46 to the positive terminal 22 of battery 20 so as to be driven as an anode and the other or reference electrode 16 is connected to the negative terminal 24 of battery 20, and a second state wherein the silver electrode 12 is connected through resistor 52 to the negative terminal 24 of the battery so as to be driven as a cathode and the other or reference electrode 16 is connected to the positive terminal 22 of the battery. When the switching means is in the first state the current flow is in a direction relative to the silver electrode 12 causing silver ions to be released to create a germicidal environment at the tissue site, and when the switching means is in the second state the current flow is in an opposite direction relative to the electrode 12 causing healing of the tissue at the site.

By way of example, in an illustrative device battery 20 delivers an output voltage of 2.8 volts, resistor 46 has a magnitude of about 150 kilohms, and resistor 52 has a magnitude of about 2 megohms. Electrode 16 is integral with the outer casing 56 or can of the battery 20 which casing 56 is of electrically conductive material such as stainless steel. Accordingly, electrode 16 operatively contacts neighboring body tissue through the contact of the casing 56 with such tissue. When switch arms 28 and 34 are moved by the magnet into positions engaging the contacts 32 and 38, respectively, the silver electrode 12 is driven as an anode and a positive germicidal current of about 15 microamperes is delivered through the electrode 12 to the tissue site. After a predetermined time the magnet is removed and the switch arms 28 and 34 move to their normal positions engaging the switch contacts 30 and 36 thereby driving the electrode 12 as a cathode. In this mode a negative healing current of about 1.0 microampere is delivered through the silver electrode 12 to the tissue site.

In one form of the apparatus, the components including the switching means, resistors 46,52 and leads are assembled and arranged on the top or lid of the battery 20 and then cast into a body of suitable epoxy material such as Scotchcast V or the equivalent. Alternatively, the battery 20 and remaining components including switches, resistors and leads are placed in another enclosure or container of metal which then is hermetically sealed. The outer metallic enclosure or container would be, for example, of titanium or stainless steel and provided with hermetic feed through terminals of glass or ceramic material. The apparatus typically is implanted in the body tissue of a patient, and should long-term implantation be considered, the anodal corrosion of the stainless steel or titanium reference electrode might be objectionable, in which case the reference electrode could be of platinum. While the present example considers the metallic casing or can as the reference electrode, the can could be left "floating" electrically and a separate reference electrode such as a platinum wire would be provided. When the apparatus is implanted in the body tissue of a patient, the switch operating magnet is externally applied to the adjacent region of the patient's body and held in place by a bandage or similar holding means. The magnet is held in position for a predetermined time, for example several days to place the apparatus in the germicidal mode. Then the magnet is removed to reverse the voltage polarity of the output of the apparatus thereby switching the operation to a healing mode. The apparatus then remains in the healing mode for the required time, which can be approximately twelve weeks for healing simple fractures to as long as up to about 12 years when controlling pseudoarthritis of the tibia bone. The latter condition occurs congentially in children and results in periodic breakage of the tibia bone. After puberty the condition spontaneously disappears.

Figure 2:
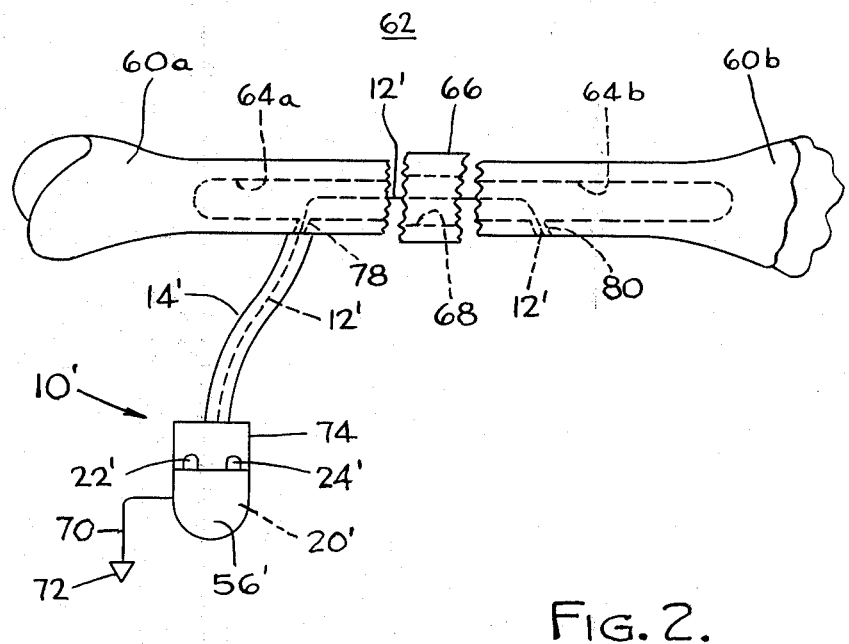
FIG. 2 is a diagrammatic view illustrating the apparatus of the present invention in a typical application wherein it is implanted in the body of a patient adjacent a bone graft site.

FIG. 2 illustrates a typical application of the apparatus of the present invention for providing germicidal and healing treatment at a bone graft site. The clinical procedures are described in further detail by Becker, Spadero and Marino in "Clinical Experiences in Low Intensity Direct Current Stimulation of Bone Growth", *Journal of Clinical Orthopedics*, 124:75, 1977. A live bone 60 which has been fractured or otherwise broken into two sections 60a and 60b is located within the body tissue 62 of a patient. The live bone sections 60a and 60b have medullary cavities 64a and 64b, respectively. Between the fractured or broken ends of the bone sections 60a and 60b there is inserted a dead bone graft section 66 which has a medullary cavity 68. The spacing between the graft section 66 and the adjacent ends of the live bone sections 60a and 60b is exaggerated for convenience in illustration. The apparatus of the present invention, generally designated 10', is implanted in the body tissue 62 of a patient at a location adjacent the bone graft site. The apparatus is similar to that shown in FIG. 1 and identical components are provided with the same reference numeral having a prime designation. Battery 20' has an outer casing 56' of metal and in this particular illustration casing 56' is connected by a lead 70 to a reference electrode 72 implanted in tissue 62 at an adjacent location. Alternatively, the battery casing 56' may itself be the reference electrode. Components of the apparatus 10' including the switching means, resistors and leads are encapsulated in a body of epoxy material 74 which is formed on the lid of battery 20' adjacent the positive and negative terminals 22' and 24', respectively. A passage or bore 78 is drilled surgically or otherwise provided in the live bone section 60a leading from the exterior surface thereof into the medullary cavity 64a, the passage 78 extending at an acute angle to the longitudinal axis of the bone section. Similarly, another passage or bore 80 is provided in the live bone section 60b extending from the external surface thereof into the medullary cavity and disposed at an acute angle to the longitudinal axis of the bone section. The silver electrode or wire 12' extends from the apparatus 10' through and along the passage 78, into and along the medullary cavity 64a in a direction toward the bone graft section 66, from the bone section 60a through the bone graft section 66 and along the medullary cavity 68 thereof, into and along the medullary cavity 64b of the other live bone section 60b, and then into the passage 80 provided in that bone section extending along the entire passage and terminating at the outer surface of the live bone section 60b. The sheet or covering 14' of protective material, such as silicone rubber, extends from the body 74 of the apparatus to the outer surface of the live bone section 60a so that this portion of the length of wire 12' is not exposed to the neighboring tissue 62. Thus, the remaining section of the silver wire 12' is entirely exposed to the live bone sections 60a, 60b and to the graft bone section 66. Alternatively, the exposed portion of wire 12' could be placed directly in the fracture site, adjacent to the areas where healing is desired. This is because it may be either the current field through the bone break or the voltage field around the electrode 12 when driven as a cathode which is most effective in promoting osteogenesis. In addition, bone chips or fragments might be used in the bone graft section 66 rather than a discrete bone segment.

After the apparatus 10' has been implanted and installed in the foregoing manner, a magnet is externally applied to the adjacent outer surface of the patient's skin over the apparatus 10'. The magnet is held in place by a bandage or other suitable fastening means as previously described. This activates the two implanted reed switches placing the apparatus in the germicidal mode of operation wherein the positive current having a magnitude of about 15 microamperes is driven into the silver electrode 12' causing anodal corrosion of the silver and the release of silver ions into the region of the bone graft. This creates a germicidal environment which clears the bone graft area of bacterial infection. This release of silver ions also possibly clears the area of tumor cells according to the findings reported by Spadero in 1976.

After a predetermined time, which can range from about one day to about one week, the external magnet is removed with the result that the reed switches move to their normal positions thereby placing the apparatus in the healing mode of operation. In this mode, the voltage output polarity of the apparatus is reversed, and the electrical current output is reduced to a level of about 1.0 microamperes and the direction of current flow is reversed. The apparatus of the present invention has 1.5 ampere hours of battery life and therefore can remain viable for over 10 years. However, after adequate healing is obtained the apparatus could either be removed or simply left implanted innocuously in the body tissue. Normal bone growth advances sufficiently to justify removal of the apparatus in about 12 weeks. Specialized cases, on the other hand, which heretofore were untreatable, could require up to 12 years of stimulation, and the apparatus of the present invention is quite capable of doing that.

Figure 3:
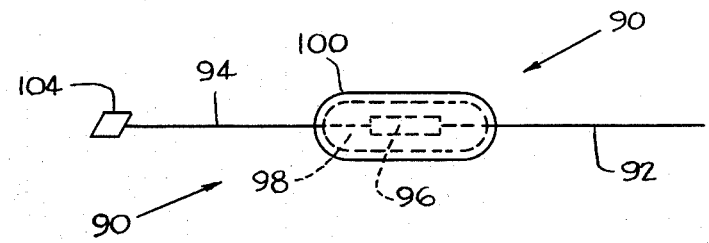
FIG. 3 is a diagrammatic view of apparatus according to another embodiment of the present invention.

FIG. 3 illustrates apparatus according to another embodiment of the present invention. In this embodiment the apparatus includes a treating electrode, another electrode, and an element which serves to form a galvanic couple with the treating electrode to create a germicidal environment at the tissue site, whereupon a predetermined time thereafter the galvanic couple changes to a biogalvanic couple with body fluid and tissue to cause healing of the tissue site. In particular, the apparatus generally designated 90 in FIG. 3 includes a treating electrode 92 adapted to be connected to a living tissue site to be healed. The treating electrode is of a material, preferably silver, which releases ions to create a germicidal environment at the site in response to electrical current flow in one direction relative to the treating electrode and which promotes healing of tissue at the site in response to electrical current flow in the opposite direction. According to a preferred mode of the present invention the electrode 92 is in the form of a thin silver wire. The apparatus includes another electrode 94 adapted to be connected to a location spaced from the site to be healed. According to a preferred mode of the present invention the other electrode 94 comprises a platinum wire. The apparatus further comprises means for establishing an electrical current flow path between the electrodes, and in the apparatus shown a resistor designated 96 is connected electrically in series between the electrodes 92 and 94. As illustrated in FIG. 3, the resistor 96, electrical terminals thereof, and portions of the wires 92,94 which are connected by soldering, welding or the like to the resistor terminals are encapsulated in a body 98 of epoxy material, for example epoxy material commercially available under the designation Scotchcast V. The body 98, in turn, is enclosed in a sheet or layer 100 of human body reaction free material, for example Dow Corning Silicon Type A medical adhesive material.

The apparatus of the present invention further comprises means for applying direct voltage of one polarity to the treating electrode 92 to cause electrical current flow in the one direction to create a germicidal environment at the tissue site and after predetermined time applying direct voltage of the opposite polarity to the treating electrode to promote healing of tissue at the site. In particular, the apparatus includes a minute quantity or body of magnesium 104 which is joined to the end or tip of the platinum electrode 94. Magnesium element 104 can be joined to the platinum wire 94 in a suitable manner, for example by dipping the end of the platinum wire 94 into a quantity of molten magnesium and then allowing the adhered quantity to cool and thereby bond to the tip of wire 94. The body of magnesium 104, being very chemically active, forms a strong galvanic couple with the silver electrode 92, initially driving the silver electrode positive as an anode to a voltage of about 1500 millivolts measured open circuit. The magnesium also is attacked by the warm physiological saline present in the body tissue. A current of about 15 microamperes is delivered through the silver electrode 92 to the tissue site, the silver corroding and leaving a germicidal environment of silver ions at the site. This corrosion together with the galvanic battery action is sufficient to consume all of the minute amount of the magnesium body 104 in a few days. The amount is so small or negligible that the residual products are carried away easily by the body circulatory system. Once the magnesium quantity 104 is consumed, the apparatus then automatically reverts to the healing mode wherein the silver wire 92 is driven as a cathode, In particular, the silver electrode 92 and platinum electrode 94 create a biogalvanic couple with the body tissue and the fluid which couple delivers about 250 millivolts measured open circuit to the silver electrode 92 which is driven as a cathode in this mode. Resistor 96 preferably has a magnitude of about 100 kilohms.

Thus, the apparatus 90 initially has an automatic germicidal mode wherein about 15 microamperes of anodal current is delivered through the silver anode 92 to the tissue site for a few days. The silver corrodes and leaves a germicidal environment of silver ions to remove any infection at the tissue site. After a few days in this mode, the electrical polarity of the output of the apparatus automatically reverses. The silver electrode 92 automatically becomes a cathode and proceeds to heal the fracture at the tissue site over the required period of time. The series resistor 96 having a magnitude of about 100 kilohms serves to limit the current to the range from about 10 microamperes to about 15 microamperes in the germicidal mode and to about 1 microampere in the opposite direction when the apparatus is in the healing mode. By way of example, the magnesium body 104 has a weight of about 15 milligrams.

Figure 4:
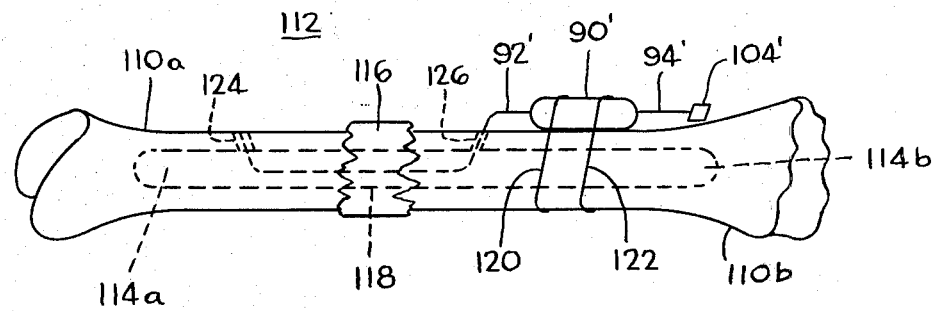
FIG. 4 is a diagrammatic view of the apparatus of FIG. 3 implanted in the body of the patient adjacent a bone graft site.

FIG. 4 illustrates the apparatus of this embodiment of the present invention in a typical application as it would appear implanted adjacent a bone graft site. A live bone 110 includes a first section 110a and a second section 110b which have been separated or broken due to a fracture. The bone 110 is within the body tissue 112 of a patient. Bone section 110a has a medullary cavity 114a and, similarly, bone section 110b has a medullary cavity 114b. Between the fractured bone sections 110a and 110b a bone graft section 116 is positioned in a manner similar to that of the arrangement of FIG. 2, the bone graph section 116 having a medullary cavity 118. The apparatus of this embodiment of the present invention, here designated 90', is anchored to the bone 110 near the fracture site. The apparatus 90' can be anchored by various suitable means, for example a pair of wires designated 120,122 in FIG. 4 which are wrapped around the bone section 110b to secure the apparatus 90' thereto. The platinum wire or electrode wire 94' extends from the body of epoxy encapsulant along and in spaced relation to the outer surface of bone section 110b as shown in FIG. 4. The magnesium body 104' at the tip of wire 94' is free to float in the neighboring body fluid. A first bore or passage 124 is provided surgically in bone section 110a extending from the outer surface thereof to the medullary cavity 114a and disposed at an acute angle to the longitudinal axis of bone section 110a. Similarly, a bore or passage 126 is provided in bone section 110b extending from the outer surface thereof to the medullary cavity 114b thereof and disposed at an acute angle to the longitudinal axis of the bone section 110b. The silver electrode or wire 92' of the apparatus extends from the body of encapsulant through and along the passage 126 to the medullary cavity 114b, further along in a direction toward the bone graft section 116 through the medullary cavity 18 thereof, and into the medullary cavity 114a of bone section 110a. The wire 92' extends further along the medullary cavity 114a and then enters and extends along the passage 124 in bone section 110a. The wire 92' terminates adjacent the outer surface of the bone section 110a. Alternatively, bone chips or fragments might be used in the bone graft section 116 rather than a discrete bone segment.

Figure 5:
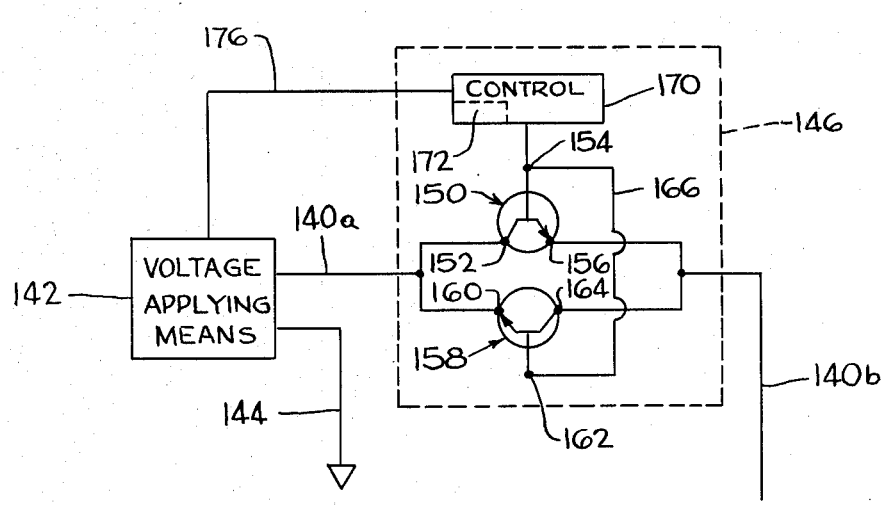
FIG. 5 is a schematic diagram of a monitoring scheme useable with the apparatus of the present invention.

FIG. 5 illustrates a monitoring arrangement for use with apparatus of the type illustrated in FIGS. 1-4. In particular, tissue growth control apparatus of the type illustrated in FIGS. 1-4 operate with low level d.c. currents, and this low level d.c. current operation renders implanted devices of this type difficult if not impossible to monitor by means of conventional external patient monitoring apparatus and procedures. In accordance with the present invention, a wave shaping circuit is operatively associated with the treating electrode to facilitate external monitoring of the apparatus when implanted. Referring now to FIG. 5 there is shown implantable apparatus for healing treatment of tissue such as bone comprising a treating electrode 140 of a material which promotes healing of tissue in response to electrical current flow relative to the electrode, and means generally designated 142 for applying voltage to the electrode to cause the current flow. For example, the combination of treating electrode 140 and voltage applying means 142 can represent the apparatus designated 10 in FIG. 1. In the arrangement of FIG. 5, the treating electrode, for example a thin silver wire as described in the previous embodiments, is shown in two sections 140a and 140b. The apparatus also includes another electrode 144 which is in a current flow path including the treating electrode 140 and is applied to a location spaced from the site to be healed. In accordance with this embodiment of the present invention, there is provided wave shaping means generally designated 146 operatively connected to the voltage applying means 142 and to the treating electrode 140 for causing the electrical current flow relative to the treating electrode to have a wave form which is readily discernable by external patient monitoring apparatus. The wave shaping means 146 includes switching means connected between the voltage applying means 142 and the treating electrode 140 for alternately connecting and disconnecting the voltage applying means to the treating electrode, and control means connected in controlling relation to the switching means for operating, i.e. opening and closing, the switching means. In an illustrative form of wave shaping means, the switching means includes a first transistor switch 150 having collector, base and emitter terminals 152, 154 and 156, respectively. Collector terminal 152 is connected to the section 140a of the treating electrode and emitter terminal 156 is connected to the section 140b of the treating electrode. In order to accomodate flow of current in two directions, as in the embodiment of FIG. 1, the switching means further includes a second transistor switch 158 having emitter, base and collector terminals 160, 162 and 164 respectively. Emitter terminal 160 is connected to the section 140a of the treating electrode and collector terminal 164 is connected to the section 140b of the treating electrode. The control or base terminals 154 and 162 of the transistor switches 158 and 150, respectively, are connected together by a lead 166, and are connected in turn to the output of a control means generally designated 170. Control means 170 provides output control pulses which are transmitted to the base terminals 154 and 162 for turning the transistor switches 150 and 158 on and off at a controlled rate in a known manner. The control means 170 includes timing means 172 for controlling the duration of the control pulses. In other words, the combination of the control means and timing means, which for example can be a multivibrator type circuit having RC timing control, opens and closes the transistor switches 150 and 158 at a controlled rate. In accordance with a preferred mode of the present invention, the switches are turned on and off about once each second with the on time duration being about twice the length of the off time duration. The resulting current wave form through the treating electrode 140 has leading and trailing edges which are clearly discernable by external patient monitoring apparatus. Voltage for operating the control means 170 in the present illustration is obtained from component 142 by means of line 176.

In order to monitor operation of the implanted tissue growth control apparatus, the shaped wave form of the electrical current flowing relative to the treating electrode 140 is detected by means of monitoring apparatus external to the body of the patient and responsive to the shaped wave form. For example, the leading and trailing edges of the on-off current wave form are clearly discernable on a conventional ECG machine. In addition, the operation of the apparatus can be monitored on an oscilloscope provided with skin electrodes which would be located on the external skin of the patient, one over the area or site to which the treating electrode 140 is connected and the other skin electrode over the region where the reference electrode 144 is connected. Thus, one can readily determine that the implanted apparatus continues to operate. In addition, the mode of operation of the implanted healing apparatus, i.e. be it the germicidal or the healing mode as in the embodiments illustrated in FIGS. 1-4, would be clearly discernable from the wave form polarity and the magnitude and/or repetition rate of the signal detected by the apparatus. This is because the current flows are in opposite directions and also are of different magnitudes in the two modes, and in addition there could be a different repetition rate of the current in the germicidal and healing modes.

It is therefore apparent that the present invention accomplishes its intended objects. While several embodiments of the present invention have been described in detail, this is for the purpose of illustration and not limitation.

I claim:

1. Apparatus for implantation in a patient for providing germicidal and healing treatment of tissue such as bone comprising:

(a) an electrode of silver adapted to be operatively connected to a living tissue site to be healed;

(b) another electrode adapted to be connected to a location spaced from the site to be healed;

(c) a source of direct voltage having positive and negative polarity output terminals;

(d) switching means operatively connected to said electrodes and to said terminals of said source, said switching means having a first state wherein said silver electrode is connected to said positive terminal and said other electrode is connected to said negative terminal once during an initial portion of the time during which said silver electrode is operatively connected to the tissue site and a second state wherein said silver electrode is connected to said negative terminal and said other electrode is connected to said positive terminal once during the remaining portion of the time during which said silver electrode is operatively connected to the tissue site, said switching means including means enabling said switching means to be operated by operator means positioned external to said patient at a location so as to be operatively associated with said switching means for selectively and non-invasively changing the states of said switching means; and (e) means for enclosing said source, said switching means, any portion of said silver electrode not in operative contact with said tissue site to be healed, and any portion of said other electrode not in operative contact with said location spaced from the site to be healed, said enclosing means being of human body reaction free material thereby permitting said apparatus to be implanted in the body of the patient;

(f) whereby when said switching means is in said first state current flow is in a direction relative to said silver electrode causing silver ions to be released to create a germicidal environment at the tissue site and when said switching means is in said second state current flow is in an opposite direction causing healing of tissue at the site.

2. Apparatus according to claim 1, wherein said switching means comprises a pair of single pole double throw magnetic reed switches and wherein said operator means comprises a magnetic element operatively associated with said switches for selectively changing the states of said switches.

3. Apparatus according to claim 1, wherein said direct voltage source comprises a battery.

4. Apparatus according to claim 3, wherein said battery is of the lithium-halogen type.

5. Apparatus according to claim 1, wherein said silver electrode comprises a silver wire adapted to be inserted in the tissue site.

6. Apparatus according to claim 1, further including first electrical resistance means connected between said positive source terminal and said switching means and second electrical resistance means connected between said negative source terminal and said switching means, said second resistance means having a magnitude significantly greater than the magnitude of said first resistance means whereby the magnitude of current flow during healing of tissue is significantly less than the magnitude of current flow during germicidal treatment.

7. Apparatus according to claim 1, further including wave shaping means operatively associated with said silver electrode for causing the electrical current flow relative to said silver electrode to have a waveform which is readily discernible by external patient monitoring apparatus.

8. A method of providing germicidal and healing treatment of tissue such as bone comprising the steps of:
(a) providing apparatus comprising an electrode of silver adapted to be operatively connected to a living tissue site to be healed, another electrode adapted to be connected to a location spaced from the site to be healed, a source of direct voltage having positive and negative polarity output terminals, switching means operatively connected to said electrodes and to said terminals of said source, said switching means having a first state wherein said silver electrode is connected to said positive terminal and said other electrode is connected to said negative terminal once during an initial portion of the time during which said silver electrode is operatively connected to the tissue site and a second state wherein said silver electrode is connected to said negative terminal and said other electrode is connected to said positive terminal once during the remaining portion of the time during which said silver electrode is operatively connected to the tissue site, and means for enclosing said source, said switching means, any portion of said silver electrode not in operative contact with said tissue site to be healed, and any portion of said other electrode not in operative contact with said location spaced from the site to be healed, said enclosing means being of human body reaction free material whereby said apparatus is implantable in the body of a patient;
(b) implanting said apparatus in the body of a patient in neighboring relation to the tissue site to be healed including applying said silver electrode to the site and applying said other electrode to a location in the body spaced from the site to be healed;
(c) providing operator means having an operative association with said switching means for non-invasive and selective changing of the states of said switching means; and
(d) placing said operator means at a position external to the body of a patient at a location providing said operative association and operating said operator means to apply to said silver electrode for a predetermined time and once while said silver electrode is applied to the tissue site a d.c. voltage of a positive polarity causing current flow in one direction to drive said silver electrode as an anode and release ions to create a germicidal environment at the site and then to apply to said silver electrode after said predetermined time and once while said silver electrode is applied to the tissue site a d.c. voltage of opposite polarity causing current flow in the opposite direction to drive said silver electrode as a cathode to stimulate healing of tissue at the site.

9. A method according to claim 8, wherein said step of applying a d.c. voltage of opposite polarity to stimulate healing is performed for a length of time significantly greater than said step of applying d.c. voltage to create the germicidal environment.

10. A method according to claim 8, further including limiting the magnitude of current flow in said opposite direction during healing to a magnitude significantly less than the magnitude of current flow in said one direction creating the germicidal environment.

11. In combination with implantable apparatus for providing germicidal and healing treatment of tissue such as bone comprising a treating electrode of a material which creates a germicidal environment and promotes healing of tissue in response to current flow relative to the electrode, the germicidal or healing mode being determined by a characteristic of said current flow, and means for applying voltage to said electrode to cause said current flow: wave shaping means operatively connected to said voltage applying means and to said treating electrode for causing the electrical current flow relative to said treating electrode to have a waveform which is readily discernible by external patient monitoring apparatus for determining non-invasively continued operation of said apparatus when implanted and the germicidal or healing treatment mode of operation of said apparatus.

12. The combination according to claim 11, wherein said wave shaping means comprises:
(a) switching means connected between said voltage applying means and said treating electrode for alternately connecting and disconnecting said voltage applying means to said treating electrode; and
(b) control means connected in controlling relation to said switching means for opening and closing said switching means.

13. The combination according to claim 12, wherein said control means includes timing means for controlling the relative time durations of opening and closing of said switching means.

14. A method of monitoring the operation of apparatus implanted in a patient for healing treatment of tissue such as bone including a treating electrode of a material which promotes healing of tissue in response to current flow relative to the electrode, the treating electrode being applied to a tissue site to be healed and another electrode in a current flow path including the treating electrode being applied to a location spaced from the site to be healed, and means for applying voltage to the treating electrode for causing the electrical current flow relative to the treating electrode, said monitoring method comprising:
(a) shaping the waveform of the electrical current relative to the treating electrode to have a waveform which is readily discernible by external patient monitoring apparatus; and
(b) detecting the shaped waveform non-invasively by means of monitoring apparatus external to the body of a patient and responsive to the shaped waveform.

15. The method according to claim 14, wherein said step of shaping the waveform comprises periodically connecting and disconnecting the voltage applying means to the treating electrode.

16. The method according to claim 15, wherein the connecting and disconnecting is performed at a rate of about once per second.

17. The method according to claim 16 wherein the time duration of the connecting is about twice the time duration of the disconnecting.

* * * * *